United States Patent [19]

Herman

[11] Patent Number: 5,343,861
[45] Date of Patent: Sep. 6, 1994

[54] DISPOSABLE TONOMETER COVER WITH FLUORESCEIN DYE

[76] Inventor: Wesley K. Herman, 5421 La Sierra Dr., Dallas, Tex. 75231

[21] Appl. No.: 884,789

[22] Filed: May 18, 1992

Related U.S. Application Data

[63] Continuation-in-part of Ser. No. 335,237, Apr. 10, 1989, Pat. No. 5,113,863.

[51] Int. Cl.$^5$ ............................................. A61B 3/16
[52] U.S. Cl. .................................. 128/652; 206/363; 206/438
[58] Field of Search ............................... 128/645–652, 128/736; 604/263; 206/305, 306, 316.1, 363, 438; 374/158, 209

[56] References Cited

U.S. PATENT DOCUMENTS

| | | |
|---|---|---|
| 3,228,741 | 1/1966 | Becker . |
| 3,301,131 | 1/1967 | Benford . |
| 3,338,090 | 8/1967 | Coombs, Jr. et al. . |
| 3,426,749 | 2/1969 | Jephcott . |
| 3,794,091 | 2/1974 | Ersek et al. . |
| 4,197,947 | 4/1980 | Zaidi . |
| 4,200,110 | 4/1980 | Peterson et al. ................... 128/634 |
| 4,213,464 | 7/1980 | Katz et al. . |
| 4,444,310 | 4/1984 | Odell . |
| 4,511,035 | 4/1985 | Alpern . |
| 4,599,901 | 7/1986 | Hirschfield ......................... 73/705 |
| 4,602,642 | 7/1982 | O'Hara et al. ...................... 128/736 |
| 4,669,610 | 6/1987 | Lindsey et al. . |
| 4,730,726 | 3/1988 | Holzwarth . |
| 4,790,569 | 12/1988 | Chaffee . |
| 4,922,914 | 5/1990 | Segal et al. ........................ 128/646 |

*Primary Examiner*—Randy C. Shay
*Attorney, Agent, or Firm*—Crutsinger & Booth

[57] ABSTRACT

A cover and packaging and method for use in preventing infection in applanation tonometry eye testing. The cover has a circular transparent portion, a frustum shaped mounting portion and a frustum shaped handling flange. It is sterile, disposable, unitarily dispensable, and fits onto existing standard applanation tips. The circular transparent portion of the cover has an effective amount of a photoactive agent therein for enhancing the view of the calibration image during the pressure measurement.

20 Claims, 2 Drawing Sheets

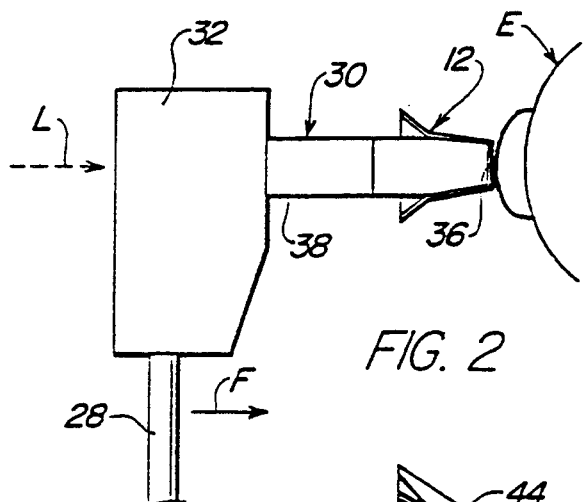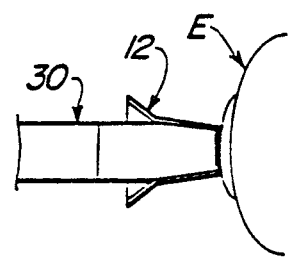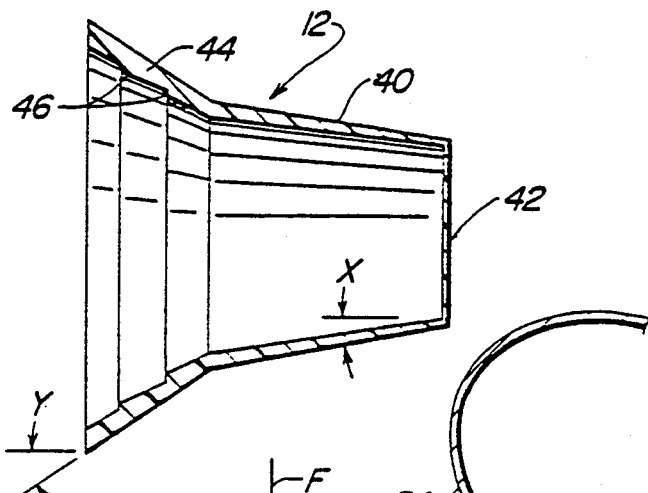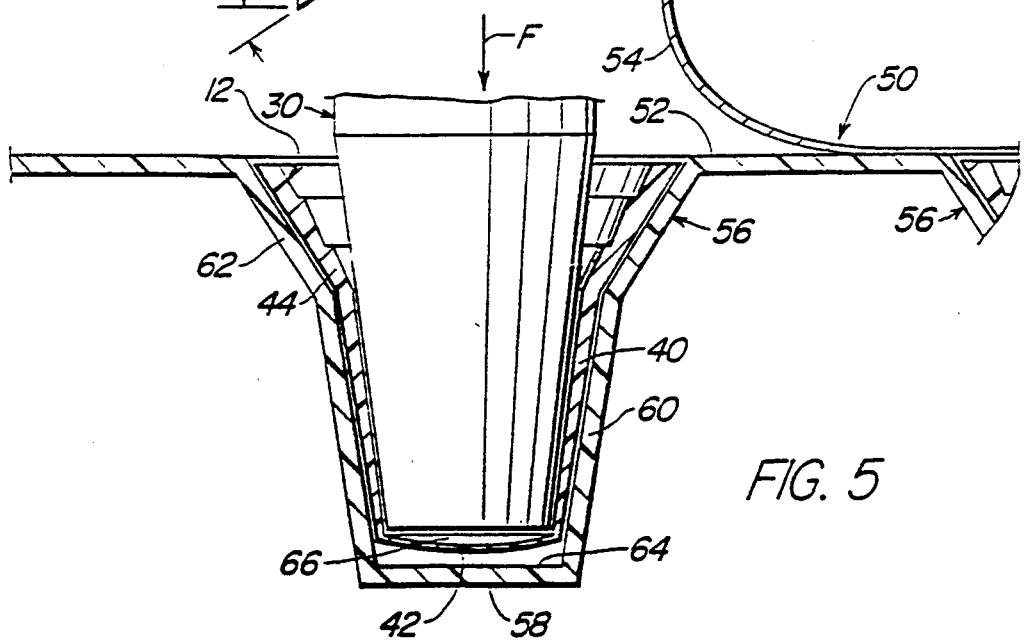

DISPOSABLE TONOMETER COVER WITH FLUORESCEIN DYE

CROSS REFERENCE TO RELATED APPLICATION

This is a continuation-in-part of U.S. Pat. application filed Apr. 10, 1989, Ser. No. 07/335,237, entitled DISPOSABLE OCULAR DIAGNOSIS DEVICE AND METHOD.

FIELD OF THE INVENTION

The present invention relates to the prevention of the spread of infection during ophthalmic testing and more particularly to a disposable sterile cover for equipment used in measuring pressures within the eye.

BACKGROUND OF THE INVENTION

The pressure within the eye has long been regarded as a significant clue in assessing the health of the eye. Physicians in Egypt and Greece, our earliest recorded civilizations, have regarded the hardness or pressure of the eye as being indicative of vision threatening eye disease. Initially, pressure was assessed with digital applanation. By this technique, the eye was balloted gently between opposing fingers of the left and right hand, and judgment was made by the clinician as to normal or abnormal pressure. Digital tonometry continued in practice throughout the early evolution of ophthalmology. Modern ophthalmic surgeons are familiar with the application of digital tonometry and can quite readily tell the difference between normal or abnormal pressures of moderate magnitudes.

The present uses of tonometry respect and honor age old traditions of digital tonometry. It is first and foremost important to know whether the pressure is normal or whether the pressure is significantly out of range from normal. This relates to both high and low pressures. However, the accumulation of accurately measured serial data over a patient's ocular history allows trending of pressures and frequently accurate prediction of certain pressure related events which may be vision threatening. Intraocular pressure is important in the differential diagnosis of acute eye problems. It is often important to measure the intraocular pressure in an eye which otherwise may have acute inflammatory, viral, bacterial, ischemic, or traumatic etiologies. Intraocular pressures also need to be measured in the immediate post-operative period when intraocular contamination is at greatest risk. A sterile instrument is thus desirable. Careful slit lamp biomicroscopic observation during the acquisition of applanation tonometry also allows a direct view of the intraocular pulse through the mires of the applanation device. This observation has significance in accessing carotid and intracranial blood flow and ocular perfusion.

The evolution of the ophthalmic subspecialty as a scientific as well as an artful practice, however, required standardization and quantification of these measurements. Consequently, one of the first biometric parameters to be utilized was tonometry. Schiotz tonometry is a mechanical, non optical gravity dependent device which measures intraocular pressures by using a metallic weighted probe to indent the cornea with the patient in a supine position. Although very small variations in weight are significant, accuracy has been found to be reproducible. Intraocular pressure curves and distributions of intraocular pressure within normal populations have been formulated. Normal and abnormal ranges and standards have been identified. This important biometric data accumulation has founded the basis for investigation into the etiology and treatment of glaucoma, a disease whereby the intraocular pressure damages the optic nerve.

The means for increased convenience of obtaining this measurement followed the introduction of the slit lamp biomicroscope, and additional forms of pressure measurement were developed. In particular, what is known in the profession as the Goldmann applanation tonometer was designed for use at the stereo, slit lamp biomicroscope for pressure measurement convenient and comfortable to both patient and physician. The Goldmann device currently is the most widely used instrument for determining intraocular pressures and is supplied by Haag Sterit Ag. Ophthalmological Instruments, 3097 Liedefeld, Berne, Switzerland. The Goldmann device uses an applanation tip which is supported on an arm attached to a slit lamp biomicroscope. It is placed in contact with the surface of the cornea with the patient in the seated position. By use of a slit lamp, the technician views the tip-cornea contact area while varying the applied force on the tip to flatten the cornea. When the flattened corneal area coincides with a standard calibration image of the tip, the force measured is recorded. Viewing of the calibration image is enhanced by applying a fluorescein dye to the cornea.

Even though forces of small magnitude are involved, the accuracy of applanation tonometry is excellent. It is recognized as the international standard to which all other measurements are compared. Applanation tonometry by the Goldmann technique is the standard initial screening for intraocular pressure related problems.

This very beneficial tonometry process also carries with it certain recognized disadvantages. It is recognized that bacterial and viral infections have been spread through patient contact with infected tonometers. It is known, for example, that viral and bacterial infections can be spread fomitically. The applanation tip is a carrier of these contaminants. Adenovirus of several strains is readily transmissible by tear or mucus membrane contact. Hepatitis is likewise known to be present in the aqueous secretion of tears and it is likely that inoculation to a second patient is not only possible but probable. The active AIDS virus has been identified in tears as well as in other glandular secretions.

To avoid infection, attempts have been made to sterilize the applanation tip between uses. Sterilization methods have not been entirely successful, in that they are not reliable, especially with viral infections. Second, disinfectant can itself cause problems. Commercially available hydrogen peroxide of the type used with contact lenses has been used; however, there are reported cases of corneal toxicity caused by use of hydrogen peroxide to sterilize an applanation tip. Residues of common disinfectants such as household bleach, isopropyl alcohol or acetone can immediately desiccate and/or injure the corneal epithelium. In addition, repeated sterilization of the sensitive applanation tip will damage the tip.

In applications of community screenings and portable tonometry clinics, it is impractical, if not impossible, to perform these time consuming disinfectant processes. Thus, there is an urgent need for a practical means to prevent the spread of infection in tonometry testing.

SUMMARY OF THE INVENTION

According to the present invention, a disposable cover for an applanation tip is provided. The cover is unitarily formed from transparent material suitable for direct contact with a patient's eye. The material is flexible and conforms closely to the applanation tip so that it will stretch over the tip and will be held in place by the resiliency of the material during the eye testing procedure. The material is transparent and forms a circular eye contact portion covering the optically transparent area of the applanation tip. This separates the tip from the eye and prevents contamination of the tip through contact with the eyelids or lashes. Surprisingly, the cover is designed so that the optical characteristics of the tip are not materially affected. A flange is formed on the cover for use in manipulating removal from the tip. The cover is designed to be installed without having to be grasped or contacted by hand, thus eliminating hand contamination of the cover.

An effective amount of a photoactive agent, such as fluorescein dye, may be introduced directly into the uncured transparent material used to form the unitary body of the disposable tonometer cover. Preferably the photoactive agent is added to the circular transparent portion of the tonometer cover so that the agent does not block too much of the light required for an accurate applanation measurement with the disposable cover. The method of making a disposable cover with a photoactive agent involves mixing the photoactive agent into the silicone prior to curing the silicone in a tonometer mold.

BRIEF DESCRIPTION

The present invention will be more easily understood from the following detailed description of the preferred embodiment when taken in conjunction with the attached drawings in which:

FIG. 2 is an enlarged partial sectional view showing a patient's eye in the initial contact position with the ocular diagnosis device of the present invention;

FIG. 3 is a view similar to FIG. 2 showing flattening of the cornea by the ocular diagnosis device;

FIG. 4 is an enlarged sectional view of the ocular diagnosis device of the present invention; and FIG. 5 is an enlarged section view illustrating the method of installation of the disposable diagnosis device on an applanation tip.

DESCRIPTION OF THE PREFERRED EMBODIMENT

Figure 1:
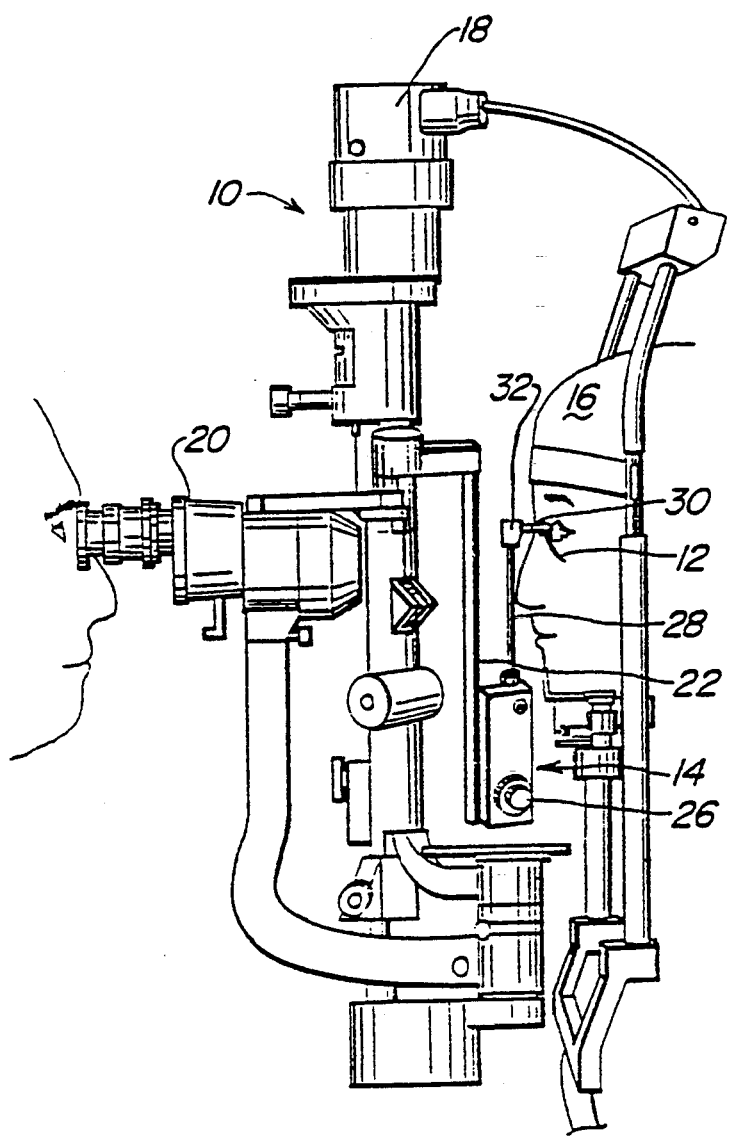
FIG. 1 is an elevation view of eye testing equipment using a disposable ocular diagnosis device of the present invention.

Referring to the drawings wherein like reference characters designate like or corresponding parts throughout the several views, there is illustrated in FIG. 1 a slit lamp type eye examination device which for purposes of description is generally identified by reference charterer 10. The slit lamp 10 is illustrated in FIG. 1 used in conjunction with the disposable ocular diagnosis device or cover 12 of the present invention. For purposes of illustration, cover 12 is shown with the slit lamp Model 900BM distributed by Haag-Streit A.G., 3097 Liedefeld, Switzerland. Slit lamp 10 is used with an applanation tonometer 14 of the Goldmann type which is also available from Haag-Streit A.G. as Model #900. It should be understood of course that the Haag-Sterit equipment is described in the present application for purposes of illustration of the environment in which the disposable sterile cover of the present invention is used and that the present invention has applications with other types of applanation equipment. In the applanation equipment illustrated in FIG. 1, the patient 16 is shown with the forehead and chin resting on the equipment to prevent head movement. A light source 18 projects a beam of light into a prism (not shown). The prism reflects the light onto the eye of the patient. The doctor or technician conducting the test examines and views the prism through a microscopic type lens system 20.

Applanation tonometer 14 is supported by arm 22. Tonometer 14 is positioned in the light path and in contact with the surface of the cornea. Applanation tonometer 14 has a base 24 and a calibrated dial 26 thereon. An arm 28 extends upward from the base and removably supports the applanation tip 30 from a mounting bracket 32.

Applanation tip has a circular cross section with a reduced diameter lens portion 36 on one end and a cylindrical mounting portion 38 at the other end (See FIG. 2). Mounting bracket 32 has a bore extending therethrough into which the mounting portion 38 is removably mounted. Thus, the light path "L" extends through the bracket 32 and applanation tip 30 and onto the eye "E" of the patient. As can be seen according to the present invention, cover 12 mounts on the applanation tip 30 to prevent contact between the eye and tip 30.

In eye testing, the position of the applanation tonometer on the patient's eye is adjusted until it is positioned as shown in FIG. 2. During this positioning procedure some relative movement between the tonometer and the cornea occurs. The cover 12 must be held on the tip to prevent dislodgement or movement during this initial positioning process. The tonometer tip in the Goldmann type device has a calibration image formed in the optics thereof. This image can be viewed by the doctor or technician along with light path "L". The tonometer tip 30 is then moved in the direction toward the eye to deform and flatten the corneal surface (see FIG. 3) until the contact between the tonometer tip and the outer surface of the eye completely fills the surface applanation area. The force applied to the tonometer tip 30 in the direction of arrow F (see FIG. 2) is measured, and through prior calibration, the internal eye pressure can be determined. In the Goldmann type tonometer, dial 26 is calibrated and by turning the dial force can be progressively applied through the arm 28 to the tonometer tip in the direction of arrow F. The forces applied to the tonometer tip to deform the eye surface are of a very small magnitude and thus, the equipment is fragile and must be handled with care.

To use the present invention, the tip 30 is removed from the mounting bracket 32. The cover 12 is installed on the tip 30 as will be described herein in greater detail. The tip 30 with cover 12 thereon is placed in the mounting bracket 32 before the patient's head is positioned in the equipment. Due to the fact that the cover 12 is made from transparent material, the applanation testing can be performed without the tip 30 itself coming into contact with the patient's eye. As can be seen in FIG. 2, the cover 12 not only covers the lens portion 36 of the applanation tip but it also extends back along the tip a sufficient distance to eliminate the possibility of the patient's eyelids or lashes contacting the tip during the positioning or testing procedure. Once testing of a patient is complete, the cover can be removed and disposed of.

The details of the structure of cover 12 are shown in FIG. 4. According to the present invention, the cover is constructed from an optically neutral transparent plastic material such as optical silicone compounded by Airmec Incorporated, 2102 Vanco Drive, Irving, Tex. 75061, Silicone Compound #10R45-1. It is anticipated that other acceptable compounds could be used. In the illustrated embodiment, the cover has a frustum shaped mounting portion 40 tapering at an angle X which preferably is 7.75 degrees. The taper of portion 40 is selected to be slightly greater than the taper of tip 30. Portion 40 is preferably designed to have a diameter at the larger end to cause a slight interference fit with the corresponding portion of tip 30. Portion 40 has a circular transparent portion 42 integrally formed on its smaller end. Transparent portion 42 is preferably sized to correspond to the smaller end of tip 30. A handling flange 44 is integrally formed to the larger or base end of the mounting portion 40. In the preferred embodiment, flange 44 is in the form of a frustum tapering at angle Y which is preferably 30 degrees. The magnitude of angle Y is selected to cause the flange 44 to extend away from tip 30 to provide access to flange 44 during removal and installation. Flange 44 has a plurality of annular stiffening ridges 46 formed therein to assist its rigidity. It is to be understood that flange 44 could be made in other shapes and its stiffness could be enhanced in other ways.

Preferably, the circular transparent portion 42 has a thinner wall than either the mounting portion 40 or handling flange 44. The circular transparent portion 42 is preferably about 0.005 inches thick; however, it is believed to perform within a range of 0.002 to 0.012 inches thick. The wall of frustum shaped portion 40 is shown varying in cross section. The portion 40 tapers from its thinnest wall adjacent the portion 42 to its thickest wall adjacent handling ring 44. In the preferred embodiment, portion 40 has a thickness of from 0.010 to 0.020 inches.

The fluorescein dye is introduced into the uncured silicone used to form the unitary body of the disposable tonometer cover 12. The tonometer cover 12 with the dye formed in the silicone may be made by mixing a ten percent aqueous solution of fluorescein sodium dye into the silicone prior to curing the silicon in the mold. If, however, the silicone becomes saturated with the fluorescein dye solution at a concentration of the dye in the silicone that is too low for accurate eye applanation measurements, an effective amount of a substantially pure powdered solid fluorescein dye may be mixed into the silicone prior to curing.

When the tonometer cover 12 is formed with dye throughout the silicone body of the cover 12, it may in some instances block too much of the light required for an accurate applanation measurement with the tonometer cover 12. Therefore, in the most preferred embodiment of the invention, an effective amount of the powdered fluorescein dye is introduced into the circular transparent portion 42 of the disposable tonometer cover 12 so that the mounting portion 40 remains substantially free of the dye.

An effective amount of the fluorescein dye may be introduced into the circular transparent portion 42 of the tonometer cover 12 during the manufacturing process. The method of manufacture involves the use of mold forms for the tonometer cover 12 and injection molding equipment. First, blocks are inserted into the tonometer mold and the mold is closed to create a molding volume conforming to the circular transparent portion 42 of the tonometer cover 12. Second, a mixture of silicone with a dispersion of an effective amount of powdered fluorescein dye is injected through one or more sprew gates into the circular transparent portion of the tonometer mold. Third, the mold is opened, the blocks are removed from the mold, and the mold is closed again. Fourth, silicone is injected through one or more sprew gates into the previously blocked portion 42 of the mold that conforms to the rest of the tonometer cover 12. The newly injected silicone will contact and bond upon curing to the previously injected silicon with fluorescein dye.

The silicone is injected into the mold at pressures as high as three thousand pounds per square inch so that every part of the mold is completely filled with silicone. The temperature of the mold is maintained between about 280 degrees to about 320 degrees Fahrenheit for curing the silicone. Therefore, the third and fourth steps of the above described process should preferably be performed quickly, before the silicone in the circular transparent portion 42 of the mold becomes completely cured, otherwise the two portions of silicone may not properly bond together to form the unitary body of the tonometer cover 12.

The curing of the silicone is completed in the mold to produce a unitarily formed tonometer cover 12 having an effective amount of the fluorescein dye in the circular transparent portion 42. Once the tonometer cover 12 is properly cured, it is removed from the mold and packaged for distribution. The method of manufacturing the tonometer cover 12 may be further improved if a suitable release agent is initially applied to the mold surfaces so that after curing the tonometer cover 12 may be more easily removed from the mold.

In FIG. 5, the cover 12 is shown in its cooperating sterile packaging assembly 50. According to a feature of the present invention, the packaging assembly 50 cooperates with the cover 12 to assist in the mounting of cover 12 on tip 30. Packaging assembly consists of a semi ridged base 52 and a sealing cap 54. Base 52 can be formed from suitable material such as high impact styrene or the like. Base 52 is formed from a flat sheet to have a plurality of receptacles 56 formed therein, each of a size and shape to receive the tip 12 therein. Receptacle 56 has a flat circular bottom portion 58, whose inside surface corresponds to the outside surface of the transparent portion 42. Receptacle 56 also has a frustum shaped portion 60 which corresponds in shape to the exterior surface of mounting portion 40. In addition, receptacle 56 corresponds in shape to a portion of the exterior of cap 12 and preferably has a frustum shaped portion 62 exactly corresponding in shape to the exterior of mounting portion 44.

To use the packaging 50, cap 54 is pealed back as shown in FIG. 5 to open one receptacle 56. The cover 12 had been previously sterilized and sealed in the receptacle 56. (Sterile pharmaceuticals used for tonometry may be packaged within, or photo active agents such as fluorescein dye may be added into the tip.) Tip 30 is inserted into the cover 12 by forcing down in the direction of arrow "F" while the bottom portion 58 rests on a work surface. As shown in FIG. 5, air 66 will be trapped inside the cover 12 by the tip 30. If the air is not completely removed, the optical path will be distorted and the eye testing could not be accurately performed. To remove the air 66, tip 30 is forced in the direction of arrow F compressing portion 42 between tip 30 and surface 58. This will remove the entrapped air. Tip 30 will have an interference with portion 40 to mount the cover 12 on tip 30. In this manner, the cover 12 can be installed on tip 30 without being handled. Removal of the cover can be accomplished by grasping the handling flange 44 with forceps or by hand. The cover will turn partially inside out.

The foregoing description of the present invention relates only to the preferred embodiment. It is to be understood that alterations and modifications can be made in the cover without departing from the spirit and scope of the invention as defined by the appending claims.

What is claimed is:

1. A disposable cover for use with a tip of applanation tonometry equipment for contacting an eye, said cover comprising: a body of flexible, optically transparent material for removably mounting on the tip, said body having a mounting portion comprising means for recovering said tip and a circular transparent portion, attached to said mounting portions said circular transparent portion having an effective amount of a photoactive material therein for enhancing the view of an image therethrough.

2. A disposable cover according to claim 1, wherein said photoactive material comprises fluorescein dye.

3. A disposable cover for use with the contacting tip of applanation tonometry equipment comprising a unitarily formed body of flexible optically transparent material for removably mounting on the applanation tip, said body having a frustum shaped mounting portion with a handling flange extending from a base end of the mounting portion and a circular transparent portion extending from and closing the end of said mounting portion, said circular transparent portion having an effective amount of a photoactive agent therein for enhancing the view of the calibration image.

4. The cover of claim 3 wherein said handling flange is frustum shaped.

5. The cover of claim 3 wherein said circular transparent portion is in the range of 0.001 to 0.012 inches thick.

6. The cover of claim 3 wherein optically transparent material comprises silicone.

7. The cover of claim 3 wherein said photoactive agent comprises fluorescein dye.

8. A disposable cover for removably mounting on an eye contacting applanation tip assembly for use in eye diagnosis to cover the tip and to prevent contact between the patient's eye and the tip thereby preventing transmission of infection between patients by the tip during use, the tip having a generally tapered shape with a larger end and a smaller eye contacting end, a circular optical lens surface formed on the smaller eye contacting end of the tip for viewing the patient's eye and for deforming the cornea surface of the patient's eye to measure the distortion of the eye and pressure within the eye, an optical path through the body of the tip and through the circular optical lens surface, said disposable cover comprising:

a unitarily formed body of flexible material;

a circular transparent portion on said body for contacting and for covering the circular optical lens surface of the tip, said circular transparent portion sized to correspond to the smaller eye contacting end of the tip, said circular transparent portion having an effective amount of a photoactive agent therein for enhancing the view of a calibration image for the pressure measurement; and a mounting portion means on said body for removably mounting said body in an interference fit on the tip and for retaining said circular transparent portion adjacent the circular optical lens surface of the tip, thereby improving the optical and contact interface between said circular transparent portion of said disposable cover and the circular optical lens surface of the tip so that distortions in the measurement of pressure within the patient's eye are minimized during use of the tip, said mounting portion means having a generally tapered shape with a larger end and a smaller end, the smaller end of said mounting means integrally formed with said circular transparent portion.

9. The disposable cover of claim 8 wherein the maximum thickness of said mounting portion means is greater than the thickness of said circular transparent portion of said disposable cover.

10. The disposable cover of claim 8 wherein the thickness of said circular transparent portion is between 0.002 inches and 0.012 inches and the thickness of the larger end of said mounting portion means is between 0.010 inches and 0.020 inches.

11. The disposable cover of claim 8 further comprising a handling flange means integrally formed on said body for handling the disposable cover, installing the disposable cover on the tip, and removing the disposable cover from the tip.

12. The disposable cover of claim 11 wherein said handling flange means diverges from the tip so that said handling flange means can be grasped without touching the tip whereby cross infection between patients is prevented.

13. The disposable cover of claim 12 wherein said handling flange means is continuous around the larger end of said mounting portion means so that said handling flange means can be grasped from any direction during installation on the tip and removal from the tip.

14. The disposable cover of claim 13 wherein said handling flange means is generally frustum shaped and tapers at an angle substantially greater than the taper of the tip so that said handling flange means extends away from the tip to provide access to said flange during installation on the tip and removal from the tip.

15. The disposable cover of claim 14 wherein said handling flange means has a plurality of annular stiffening ridges formed therein to assist its rigidity and handling strength.

16. The disposable cover of claim 11 wherein said handling flange means is continuous around the larger end of said mounting portion means so that said handling flange means can be grasped from any direction.

17. The disposable cover of claim 16 wherein said handling flange means is generally frustum shaped and tapers at an angle substantially greater than the taper of the tip so that said handling flange means extends away from the tip to provide access to said flange during installation on the tip and removal from the tip.

18. The disposable cover of claim 17 wherein said handling flange means has a plurality of annular stiffening ridges formed therein to assist its rigidity and handling strength.

19. In combination, (a) a disposable cover for an eye contacting applanation tip assembly for mounting on an eye contacting applanation tip assembly for use in eye diagnosis to cover the tip assembly and to prevent contact between the patient's eye and the tip assembly thereby preventing transmission of infection between patients by the tip assembly during use and (b) a sterile packaging assembly for said disposable cover and for assisting in mounting said disposable cover on the tip assembly, the tip assembly having a generally tapered shape with a larger end and a smaller eye contacting end, a circular optical lens surface formed on the smaller eye contacting end of the tip assembly for viewing the patient's eye and for deforming the cornea surface of the patient's eye to measure the distortion of the eye and pressure within the eye, an optical path through the body of the tip assembly and through the circular optical lens surface, wherein said disposable cover comprises: a unitarily formed body of flexible material; a circular transparent portion on said body for contacting and for covering the circular optical lens surface of the tip assembly, said circular transparent portion sized to correspond to the smaller eye contacting end of the tip assembly, said circular transparent portion having an effective amount of a photoactive agent therein for enhancing the view of a calibration image; and a mounting portion means on said body, said mounting portion means having a generally tapered shape with a larger end and a smaller end, the smaller end of said mounting means integrally formed with said circular transparent portion, said mounting portion means for removably mounting said body in an interference fit on the tip assembly and for retaining said circular transparent portion adjacent the circular optical lens surface of the tip assembly, thereby improving the optical and contact interface between said circular transparent portion of said disposable cover and the circular optical lens surface of the tip assembly so that distortions in the measurement of pressure within the patient's eye are minimized during use of the tip assembly; and said sterile packaging assembly encloses said disposable cover, said sterile packaging assembly comprising: a base of a size and shape to conform to the exterior of said circular transparent portion of said disposable cover and to conform to at least a portion of the exterior of said mounting portion means of said disposable cover; and a removable cap closing said receptacle adjacent to the larger end of said disposable cover within said base of said receptacle whereby when the removable cap is of removed, said base of said receptacle may be used by inserting the tip assembly into said disposable cover to removably mount said disposable cover on the tip assembly and to force ambient gases from the interface between the tip assembly and said circular transparent portion of said disposable cover without handling said circular transparent portion of said disposable cover and without handling said mounting portion of said disposable cover.

20. A disposable cover for use with a tip of applanation tonometry equipment for contacting an eye, said cover comprising: a unitary body of flexible, optically transparent material for removably mounting on the tip, said body having a hollow frustum shaped mounting portion with a handling flange extending from a base end of the mounting portion and a circular transparent portion extending from and closing an opposite end of said mounting portion, said circular transparent portion having an effective amount of a photoactive material therein for enhancing the view of an image therethrough.

* * * * *